US008771968B2

(12) United States Patent
Henrotin et al.

(10) Patent No.: US 8,771,968 B2
(45) Date of Patent: Jul. 8, 2014

(54) BIOMARKER FOR OSTEOARTHRITIS AND/OR OTHER AGEING-RELATED DISEASES, AND USE THEREOF

(75) Inventors: Yves Henrotin, Beaufays (BE); Myriam Gharbi, Liège (BE); Michelle Deberg, Embourg (BE); Edwin De Pauw, Marchin (BE)

(73) Assignee: Université de Liège, Angleur (BE)

( * ) Notice: Subject to any disclaimer, the term of this patent is extended or adjusted under 35 U.S.C. 154(b) by 816 days.

(21) Appl. No.: 12/737,051

(22) PCT Filed: Feb. 27, 2009

(86) PCT No.: PCT/EP2009/052392
§ 371 (c)(1),
(2), (4) Date: Feb. 22, 2011

(87) PCT Pub. No.: WO2009/146956
PCT Pub. Date: Dec. 10, 2009

(65) Prior Publication Data
US 2011/0159514 A1 Jun. 30, 2011

(30) Foreign Application Priority Data

Jun. 3, 2008 (EP) .................................... 08157521
Feb. 26, 2009 (EP) .................................... 09153804

(51) Int. Cl.
*G01N 31/00* (2006.01)
*G01N 33/53* (2006.01)

(52) U.S. Cl.
USPC ........... 435/7.21; 435/7.1; 436/501; 436/518; 424/9.1; 424/130.1; 530/300; 530/350

(58) Field of Classification Search
CPC . A61K 45/06; A61K 31/5377; C07D 401/14; C07D 471/04; C07D 487/04; C07K 14/47
See application file for complete search history.

(56) References Cited

U.S. PATENT DOCUMENTS

| | | | |
|---|---|---|---|
| 7,416,849 B2 * | 8/2008 | Allen et al. ..................... | 435/7.1 |
| 2003/0236392 A1 | 12/2003 | Isogai | |
| 2005/0287601 A1 | 12/2005 | Hageman | |
| 2006/0094054 A1 | 5/2006 | Schiemann | |

FOREIGN PATENT DOCUMENTS

| | | |
|---|---|---|
| EP | 1 764 413 | 3/2007 |
| WO | 03/063689 | 8/2003 |
| WO | 2006/006477 | 1/2006 |
| WO | 2006/052735 | 5/2006 |
| WO | 2006/138646 | 12/2006 |

OTHER PUBLICATIONS

Lecka-Czernick et al. Molecular and Cellular Biology, vol. 15, pp. 120-128, 1995.*
S. Sahebjam et al., "Increased Collagen and Aggrecan Degradation With Age in the Joints of Timp3$^{-/-}$ Mice," Arthritis and Rheumatism, Mar. 2007, vol. 56, No. 3, pp. 905-909.
D.J.C. Pappin et al., "Rapid identification of proteins by peptide-mass fingerprinting," Current Biology, 1993, vol. 3, No. 6, pp. 327-332.
I.G. Otterness et al., "An analysis of 14 molecular markers for monitoring osteoarthritis. Relationship of the markers to clinical endpoints," Osteoarthritis and Cartilage, 2001, vol. 9, pp. 224-231.
R.M. Moore et al., "Differential Expression of Fibulin Family Proteins in the Para-cervical Weak Zone and Other Areas of Human Fetal Membranes," Placenta, 2009, vol. 30, pp. 335-341.
R. Marouga et al., "The development of the DIGE system: 2D fluorescence difference gel analysis technology," Analytical and Bioanalytical Chemistry, 2005, vol. 382, pp. 669-678.
N. E. Lane et al., "Wnt Signaling Antagonists Are Potential Prognostic Biomarkers for the Progression of Radiographic Hip Osteoarthritis in Elderly Caucasian Women," Arthritis and Rheumatism, Oct. 2007, vol. 56, No. 10, pp. 3319-3325.
N. Kobayashi et al., "A Comparative Analysis of the Fibulin Protein Family: Biochemical Characterization, Binding Interactions, and Tissue Localization," The Journal of Biological Chemistry, Apr. 20, 2007, vol. 282, No. 16, pp. 11805-11816.
P. A. Klenotic et al., "Tissue Inhibitor of Metalloproteinases-3 (TIMP-3) Is a Binding Partner of Epithelial Growth Factor-containing Fibulin-like Extracellular Matrix Protein 1 (EFEMP1)," The Journal of Biological Chemistry, Jul. 16, 2004, vol. 279, No. 29, pp. 30469-30473.
L. Kevorkian et al., "Expression Profiling of Metalloproteinases and Their Inhibitors in Cartilage," Arthritis and Rheumatism, Jan. 2004, vol. 50, No. 1, pp. 131-141.
H. Kato et al., "Large-scale gene expression profiles, differentially represented in osteoarthritic synovium of the knee joint using cDNA microarray technology," Biomarkers, Jul.-Aug. 2007, vol. 12, No. 4, pp. 384-402.
P. Garnero et al., "Cross sectional evaluation of biochemical markers of bone, cartilage, and synovial tissue: metabolism in patients with knee osteoarthritis: relations with disease activity and joint damage," Annals of the Rheumatic Diseases, 2001, vol. 60, pp. 619-626.
J. Wu et al., "Comparative Proteomic Characterization of Articular Cartilage Tissue From Normal Donors and Patients with Osteoarthritis," Arthritis and Rheumatism, Nov. 2007, vol. 56, No. 11, pp. 3675-3684.
J. Devereux et al., "A comprehensive set of sequence analysis program for the VAX," Nucleic Acids Research, 1984, vol. 12, No. 1, pp. 387-395.
O. Bruyere et al., "Biochemical Markers of Bone and Cartilage Remodeling in Prediction of Longterm Progression of Knee Osteoarthritis," The Journal of Rheumatology, May 2003, obtained from http://www.jrheum.com/subscribers/03/05/1043.html, 12 pages.
D. C. Bauer et al., "Classification of osteoarthritis biomarkers: a proposed approach," Osteoarthritis and Cartilage, 2006, vol. 14, pp. 723-727.

* cited by examiner

*Primary Examiner* — Lisa Cook
(74) *Attorney, Agent, or Firm* — Jacobson Holman, PLLC.

(57) ABSTRACT

The invention relates to the identification of a biomarker whose abundance in biological sample is changed in subjects with osteoarthritis and/or other ageing-related diseases. The biomarker has applications in the diagnosis of osteoarthritis and/or other ageing-related diseases, in determining the prognosis for an individual diagnosed with osteoarthritis and/or other ageing-related diseases, and in monitoring the efficacy of treatment for osteoarthritis and/or other ageing-related diseases.

12 Claims, 8 Drawing Sheets

Figure 3A

Figure 1A:
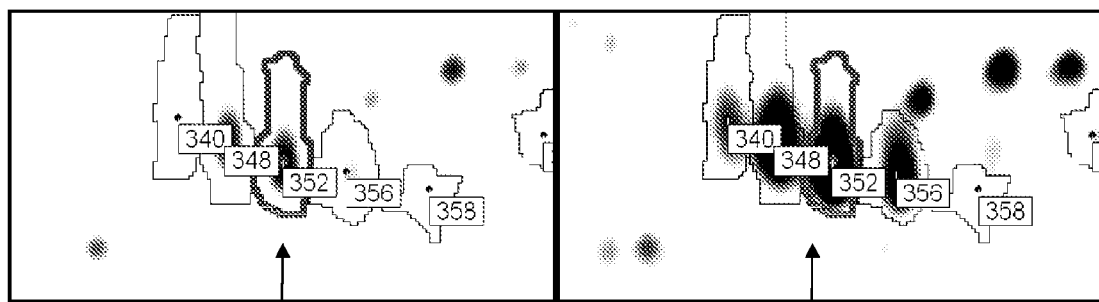

```
FBLN3_HUMAN       Mass: 54604    Score: 130    Queries matched: 2

EGF-containing fibulin-like extracellular matrix protein 1 precursor (Fibulin-3) (FIBL-3)

Query  Observed  Mr(expt)  Mr(calc)  Delta  Miss  Score  Expect   Rank  Peptide
 149    685.33   1368.64   1368.54    0.09    0     58   0.00027    1   R.CVCPVSNAMCR.E
 444    965.32   1928.63   1928.73   -0.10    0     72   4.2e-06    1   R.TCQDINECETTNECR.E
```

Figure 3B

```
         10         20         30         40         50         60
MLKALFLTML TLALVKSQDI EETITYTQCT DGYEWDPVRQ QCKDIDECDI VPDACKSGMK 70         80         90        100        110        120
CVNHYGGYLC LPKIAQIIVN NEQPQQETQP AEGTSGATTG VVAASSMATS GVLPGGGFVA 130        140        150        160        170        180
SAAAVAGPEM QTGRNNFVIR RNPADPQRIP SNPSHRIQCA AGYEQSEHNV CQDIDECTAG 190        200        210        220        230        240
THNCRADQVC INLRGSFACQ CPPGYQKRGE QCVDIDECTI PPYCHQRCVN TPGSFYCQCS 250        260        270        280        290        300
PGFQLAANNY ICVDINECDA SNQCAQQCYN ILGSFICQCN QGYELSSDRL NCEDIDECRT 310        320        330        340        350        360
SSYLCQYQCV NEPGKFSCMC PQGYQVVRSR TCQDINECET TNECREDEMC WNYHGGFRCY 370        380        390        400        410        420
PRNPCQDPYI LTPENRCVCP VSNAMCRELP QSIVYKYMSI RSDRSVPSDI FQIQATTIYA 430        440        450        460        470        480
NTINTFRIKS GNENGEFYLR QISPVSAMLV LVKSLSGPRE HIVDLEMLTV SSIGTFRTSS

490
VLRLTIIVGP FSF
```

Figure 5

TCQDINECETTNECREDEMCWNYHGGFRCYPRNPCQDPYILTPENRC
VCPVSNAMCR

Figure 6

MLKALFLTMLTLALVKSQDTEETITYTQCTDGYEWDPVRQQCKDIDE
CDIVPDACKGGMKCVNHYGGYLCLPKTAQIIVNNEQPQQETQPAEGT
SGATTGVVAASSMATSGVLPGGGFVASAAAVAGPEMQTGRNNFVIRR
NPADPQRIPSNPSHRIQCAAGYEQSEHNVCQDIDECTAGTHNCRADQV
CINLRGSFACQCPPGYQKRGEQCVDIDECTIPPYCHQRCVNTPGSFYC
QCSPGFQLAANNYTCVDINECDASNQCAQQCYNILGSFICQCNQGYEL
SSDRLNCEDIDECRTSSYLCQYQCVNEPGKFSCMCPQGYQVVRSRTC
QDINECETTNECREDEMCWNYHGGFRCYPRNPCQDPYILTPENRCVC
PVSNAMCRELPQSIVYKYMSIRSDRSVPSDIFQIQATTIYANTINTFRIK
SGNENGEFYLRQTSPVSAMLVLVKSLSGPREHIVDLEMLTVSSIGTFRT
SSVLRLTIIVGPFSF

BIOMARKER FOR OSTEOARTHRITIS AND/OR OTHER AGEING-RELATED DISEASES, AND USE THEREOF

This is a national stage of PCT/EP09/052,392 filed Feb. 27, 2009 and published in English, which has a priority of European no. 08157521.9 filed Jun. 3, 2008, and European no. 09153804.1 filed Feb. 26, 2009, hereby incorporated by reference.

The present invention relates to a biomarker for osteoarthritis and/or other ageing-related diseases. In particular, the invention relates to a method of diagnosing osteoarthritis, and/or other ageing-related diseases, by determining the level of a biomarker in a biological sample. The invention also relates to the use of a biomarker found in biological sample to monitor the efficacy of a treatment for osteoarthritis, and/or other ageing-related diseases, and to determine the prognosis for an individual diagnosed with osteoarthritis, and/or other ageing-related diseases.

Osteoarthritis is a progressive disorder characterized by destruction of articular cartilage and by subchondral bone and synovial changes. Currently the diagnosis of osteoarthritis is based on clinical and radiographic changes which occur late during disease progression. More specifically, diagnosis is based on cartilage integrity, which as articular cartilage is invisible on radiographs must be assessed indirectly from the spacing between subchondral bone ends in a joint. This method does not allow detection of early structural damage, and is cumbersome to use in daily practice.

Biochemical markers of bone, synovium or cartilage turnover have been proposed as potential tools for the diagnosis, prognosis and treatment monitoring of osteoarthritis (Garnero, P., et al., Ann Rheum Dis, 2001. 60(6): p. 619-26; Bruyere, O., et al., J Rheumatol, 2003. 30(5): p. 1043-50; and Wu, J., et al., Arthritis Rheum, 2007. 56(11): p. 3675-84). More specifically, Wu et al. (Arthritis Rheum, 2007. 56(11): p. 3675-84) describe potential molecular mediators and biomarkers of osteoarthritis in cartilage tissue. The method of Wu et al uses articular cartilage, obtained by an invasive procedure which provides only a limited amount of tissue. The method is therefore costly, time consuming and unsuitable for routine diagnostic testing, or for monitoring disease progression, or for determining the therapeutic effect of a treatment.

There therefore remains a need for a simple, rapid and effective method for the diagnosis of osteoarthritis and/or other ageing-related diseases, and/or to monitor the efficacy of treatments for osteoarthritis and/or other ageing-related diseases, and/or to determine the prognosis for a patient diagnosed with osteoarthritis and/or other ageing-related diseases.

The present invention provides a method for (i) diagnosing osteoarthritis and/or another ageing-related disease, (ii) determining the prognosis for a patient with osteoarthritis and/or another ageing-related disease, and (iii) monitoring the efficacy of a treatment for osteoarthritis and/or another ageing-related disease, using readily available biological samples and allow for rapid and cost effective use.

Reference herein to "other ageing-related diseases" or "another ageing related disease" is intended to refer to one or more diseases related to ageing which may include one or more of osteoporosis, macular degeneration and other degenerative diseases.

According to one aspect, the present invention provides a method of determining the osteoarthritis status of a subject, and/or the status of another ageing-related disease in a subject, comprising the steps of:

(i) determining the concentration in a biological sample of a free fragment comprising the same or substantially the same amino acid sequence as Seq ID no:1 or a fragment thereof;

(ii) comparing the free fragment concentration determined in step (i) with one or more reference values.

Reference herein to "free fragment" is intended to refer to a polypeptide, a peptide or otherwise released from mammalian fibulin-3 molecule by an oxidative or enzymatic processing. A free fragment is different from the native protein by its structure and configuration and may undergo modification such as phosphorylation, glycosylation or any other post-traductional modification resulting of a pathological mechanism. The free fragment according to the invention contributes to the identification of the pathologic status of osteoarthritis or osteoporotic patient.

According to another aspect, the present invention provides a method of diagnosing osteoarthritis and/or another ageing-related disease in a subject, comprising the steps of:

(i) determining the concentration in the sample of a free fragment comprising the same or substantially the same amino acid sequence as Seq ID no:1 or a fragment thereof;

(ii) comparing the free fragment concentration determined in step (ii) with one or more reference values.

According to yet another aspect, the present invention provides a method of determining the prognosis for a subject with osteoarthritis and/or another ageing-related disease, comprising the steps of:

(i) determining the concentration in the sample of a free fragment comprising the same or substantially the same amino acid sequence as Seq ID no:1 or a fragment thereof;

(ii) comparing the free fragment levels determined in step (i) with one or more reference values.

According to a further aspect, the present invention provides a method of determining the efficacy of a treatment for osteoarthritis and/or another ageing-related disease in a subject, comprising the steps of:

(i) determining the concentration in a biological sample of a free fragment comprising the same or substantially the same amino acid sequence as Seq ID no:1 or a fragment thereof;

(ii) administering a treatment for osteoarthritis and/or another ageing related disease to the subject;

(iii) determining after treatment the concentration in another biological sample of a free fragment comprising the same or substantially the same amino acid sequence as Seq ID no:1 or a fragment thereof;

(iv) comparing the free fragment concentrations determined in step (i) and step (iii) with one another, and optionally with one or more reference values.

Preferably, in any method of the invention, the concentration of a free fragment with the same sequence as the sequence of Seq ID no: 1 is determined. Alternatively, the concentration of a free fragment with a sequence substantially the same as the sequence of Seq ID no: 1 may be determined.

Alternatively, the concentration of a peptide fragment having a sequence the same, or substantially the same, as part of the sequence of Seq ID no: 1 may be determined. The peptide fragment may have a sequence the same or substantially the same as one end of the sequence of Seq ID no: 1. Alternatively, the peptide fragment may have a sequence the same or substantially the same as an internal part, that is, not including either end, of the sequence of Seq ID No: 1. Preferably the peptide fragment is at least 5, preferably at least 10, preferably at least 20, more preferably at least 30 or more amino acids long.

Preferably if the concentration of a fragment having a sequence the same, or substantially the same, as part of the sequence of Seq ID no: 1 is determined, the fragment represents an epitope within the sequence of Seq ID no: 1.

An epitope is a binding site of an antibody on an antigen. In a peptide antigen, generally a linear epitope will be at least about 7 amino acids in length, and may be at least 8, at least 9, at least 10, at least 11, at least 12, at least 14, at least 16, at least 18, at least 20, at least 22, at least 24, or at least 30 or more amino acid residues in length. However, antibodies may also recognise conformational determinants formed by non-contiguous residues on an antigen, and an epitope can therefore require a larger fragment of the antigen to be present for binding, e.g. a domain.

Reference herein to "a sequence substantially the same as" all or part of the sequence of Seq ID no: 1, refers to a free fragment with a sequence which has at least 80%, preferably at least 90%, more preferably at least 95% or 98%, sequence identity with all or part of the sequence of Seq ID No:1. Preferably the peptide has a sequence the same or substantially the same as at least about 5, 10, 15, 20, 25, 30, 35, 40, 45 or more consecutive amino acids of the sequence of Seq ID No: 1. Preferably, the free fragment has a sequence the same, or substantially the same, as the entire sequence of Seq ID No: 1.

Homology or sequence identity of two or more amino acid sequences can be measured by using a homology scoring algorithm NCBI BLAST (National Center for Biotechnology Information Basic Local Alignment Search Tool). Alternatively, the UWGCC Package provides the BESTFIT program which can be used to calculate sequence identity between two or more sequences (e.g. used on its default setting) (Devereux et al (1984) Nucleic Acids Research 12 p 387-395).

The sequence of Seq ID no:1 represents a fragment of the fibulin-3 protein. The fragment may be a degradation product of fibulin-3.

In any method of the invention the free fragment comprising a sequence the same or substantially the same as the sequence of Seq ID no: 1 or a part thereof is preferably differentially present in the sample from a subject with osteoarthritis or another ageing-related disease compared to a normal subject.

A free fragment comprising the same or substantially the same sequence as Seq ID no:1 or a fragment thereof, which is measured in step (i) and/or step (iv) in any method of the invention, is also referred to herein as the biomarker or the biomarker peptide.

Reference to the "osteoarthritis status" or to the "status of an ageing-related disease" refers to any distinguishable manifestation of osteoarthritis or an ageing-related disease, including diseased and non-diseased. For example, osteoarthritis status includes, without limitation, the presence or absence of osteoarthritis in a subject, the risk of a subject developing osteoarthritis, the stage of the disease, the progression of the disease, and the effectiveness or response of a subject to a treatment for osteoarthritis.

Any method of the invention may be used in conjunction with the assessment of clinical symptoms and/or imaging results and/or the concentration of one or more other biomarkers.

Preferably all methods of the invention are carried out in vitro.

The biological sample may comprise urine, whole blood, blood serum, blood plasma, synovium, sweat, cerebrospinal fluid, mucous, saliva, lymph, bronchial aspirate, milk and the like. Preferably the biological sample is urine.

Biological sample, such as urine, have the advantage of being abundant and easily accessible.

A further advantage of using a biological sample compared to a tissue such as cartilage, is that the progression of osteoarthritis or another ageing-related disease, and/or the therapeutic effect of a treatment, may be monitored by taking and testing samples as often as necessary without the need for invasive procedures.

The concentration of the biomarker peptide in a sample may be determined by any suitable assay. A suitable assay may include one or more of the following methods, an enzyme assay, an immunoassay, mass spectrometry, HPLC, electrophoresis or an antibody microarray, or any combination thereof. If an immunoassay is used it may be an enzyme linked immunoassay (ELISA), a sandwich assay, a competitive assay, a radioimmunoassay, a Western Blot, an immunoassay using a biosensor, an immunoprecipitation assay, an agglutination assay, a turbidity assay or a nephlelometric assay. If mass spectrometry is used it may be Matrix Assisted Laser Desorption/Ionization Time-of-Flight (MALDI-TOF) Mass Spectrometry.

Preferably the concentration of the biomarker peptide is determined using an immunoassay which uses one or more antibodies directed to the specific biomarker peptide to determine the concentration of the biomarker peptide in the sample.

If one or more antibodies are used to determine the concentration of a biomarker peptide in a sample the one or more antibodies may be synthetic, monoclonal, polyclonal, oligoclonal, bispecific, chimeric and/or humanised.

One or more of the antibodies used may comprise a tag or a label. The tag or label may be selected from the group comprising a radioactive, a fluorescent, a chemiluminescent, a dye, an enzyme, or a histidine tag or label, or any other suitable label or tag known in the art.

Preferably the reference value, to which the determined concentration of the biomarker peptide is compared, is the concentration of the same peptide in one or more "normal" subjects that do not have any detectable osteoarthritis and/or other ageing-related disease, or any clinical symptoms of osteoarthritis and/or other ageing-related disease, and have so called "normal values" of the biomarker peptide.

Alternatively, the reference value may be a previous value for the biomarker peptide obtained from a specific subject. This kind of reference value may be used if the method is to be used to monitor progression of osteoarthritis and/or another ageing-related disease, or to monitor the response of a subject to a particular treatment.

When the determined concentration of the biomarker is compared with a reference value, an increase or a decrease in the concentration of the biomarker may be indicative of the osteoarthritis status, and/or the status of another ageing-related disease, in the subject.

More specifically an increase or a decrease in the concentration of the biomarker may be indicative, or diagnostic, of osteoarthritis in the subject. An increase in the concentration of the biomarker, preferably of a free fragment with the sequence of Seq ID no:1, in a sample may be diagnostic of osteoarthritis.

Preferably an at least about 2 fold or more increase in the concentration of a free fragment with the sequence of Seq ID no:1, or with a sequence substantially the same as Seq ID no:1, or a fragment thereof, in a sample from a subject compared to a reference sample from a normal subject is diagnostic of osteoarthritis.

The method of the invention may also be used to monitor osteoarthritis progression, and/or the progression of another ageing-related disease, in a subject. Furthermore, the method of the invention may be used to monitor the efficacy of a treatment for osteoarthritis, and/or another ageing-related disease, following administration of the treatment to a subject. Efficacy of a treatment may be monitored by analysing samples taken from a subject at various time points following initiation of the treatment. By monitoring changes in the concentration of the biomarker peptide over time and comparing these concentrations to normal and/or reference values, efficacy of the treatment may be determined. In this case, reference concentrations may include the concentration of the biomarker peptide in the subject when a sample was first taken and analysed, or the concentration of the biomarker peptide in the subject when a sample was last taken, or both.

The subject in any method of the invention may be mammal, and is preferably a human, but may alternatively be a monkey, ape, dog, cow, gallus or rodent.

According to another aspect of the invention there is provided a kit for use in determining the osteoarthritis status, or the status of another ageing-related disease, in a subject, wherein the kit comprises at least one agent for determining the concentration of a free fragment comprising the same or substantially the same amino acid sequence as the sequence of Seq ID No:1, or a part thereof, in a biological sample.

The kit may be used to diagnose osteoarthritis and/or another ageing-related disease in a subject. The kit may alternatively be used to monitor disease progression or the efficacy of a treatment administered to a subject with osteoarthritis and/or another ageing-related disease.

The agent may be an enzyme, an antibody, a protein probe, a metabolite or any other suitable composition.

The agent for determining the concentration of the free fragment is preferably labelled. The kit may also comprise means for detecting the label.

The kit may comprise one or more capture agents for capturing the free fragment comprising the same or substantially the same amino acid sequence as the sequence of Seq ID No:1, or a part thereof, in a biological sample. The capture agent may be one or more antibodies. The capture agent may be an antibody according to an aspect of the invention.

The kit may comprise two antibodies for use in a sandwich assay to determine the concentration of a free fragment comprising the same or substantially the same amino acid sequence as the sequence of Seq ID No:1, or a part thereof. Preferably the kit comprises two antibodies, each directed to a different epitope on the free fragment comprising the same or substantially the same amino acid sequence as the sequence of Seq ID No: 1, or a part thereof. One antibody is preferably the capture antibody, and the other antibody is preferably a detection antibody and may be labelled to allow its detection.

The capture agent may be attached to a solid support. The solid support may be a chip, a microtitre plate, a bead or a resin.

The kit may comprise instructions for suitable operational parameters in the form of a label or separate insert. The instructions may inform a user about how to collect the sample, and/or how to wash the capture agent.

The kit may comprise samples of the biomarker peptide to be detected. The samples of the biomarker peptide may be used as a standard for calibration and comparison. The kit may also comprise instructions to compare the concentration of the biomarker peptide detected in a sample with a calibration sample or chart. The kit may also include instructions indicating what concentration of the biomarker peptide is diagnostic of osteoarthritis and/or another ageing-related disease.

According to a yet further aspect, the invention provides the use of the determination of the concentration of the biomarker peptide in a sample of biological sample as a means of assessing the osteoarthritis status in a subject or as a means of assessing the status of another ageing-related disease in a subject.

According to a yet further aspect, the present invention provides the use of a biological sample, such as urine, as a source of at least one biomarker for use in determining the prognosis of osteoarthritis progression and/or another ageing-related disease, and/or for diagnosing osteoarthritis and/or another ageing-related disease, and/or for monitoring the effect of a treatment for osteoarthritis and/or another ageing-related disease.

According to another aspect the invention provides a free fragment which comprises the same, or substantially the same, amino acid sequence as the amino acid sequence of Seq ID NO: 1, or a part thereof, or its amide, or a salt thereof.

Preferably the free fragment of the invention has a sequence the same as that of Seq ID No: 1.

According to a further aspect, the invention provides a polynucleotide encoding a free fragment according to the invention. Preferably, the polynucleotide is a DNA molecule.

According to a yet further aspect the invention provides a recombinant vector, which comprises a polynucleotide of the invention.

According to another aspect the invention provides a transformant, which is transformed with the recombinant vector of the invention.

In a further aspect, the invention provides the use of a free fragment according to the invention in the manufacture of an antibody.

It a yet further aspect, the invention provides an antibody specific for a free fragment according to the invention. In particular, the invention provides an antibody specific for a free fragment having the sequence of Seq ID No: 1.

An antibody according to the invention may be synthetic, monoclonal, polyclonal, oligoclonal, bispecific, chimeric or humanised. The antibody may be complete or a fragment thereof, such as, Fv, Fab and $F(ab)_2$ fragments. Methods of generating antibodies are well known in the art, and may include immunisation of suitable animals, such as, a rabbit, mouse, sheep or goat, with the peptide of interest (or an immunogenic fragment thereof) or recombinant techniques.

The skilled man will appreciate that preferred features of any one embodiment and/or aspect of the invention may be applied to all other embodiments and/or aspects of the invention.

Embodiments of the invention will now be described merely by way of examples with reference to the accompanying figures in which:

FIG. 1A—shows an enlargement of a portion of a 2D-DIGE map from osteoarthritis (OA) subjects (right) and non-osteoarthritis (NO) subjects (left).

Figure 1B:
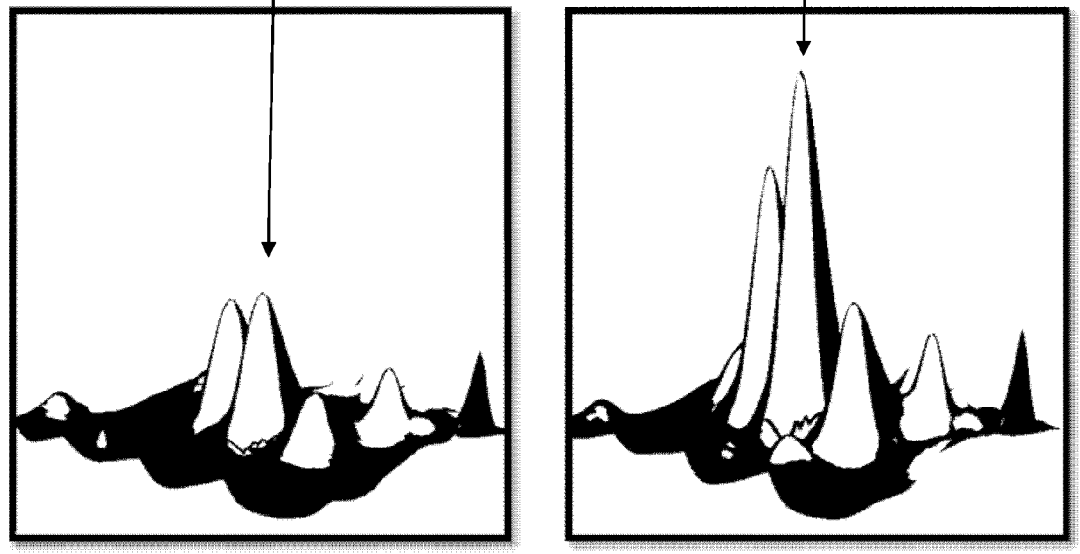

FIG. 1B—shows a representation of spot volume variation between OA subjects (right) and NO subjects (left).

Figure 2:
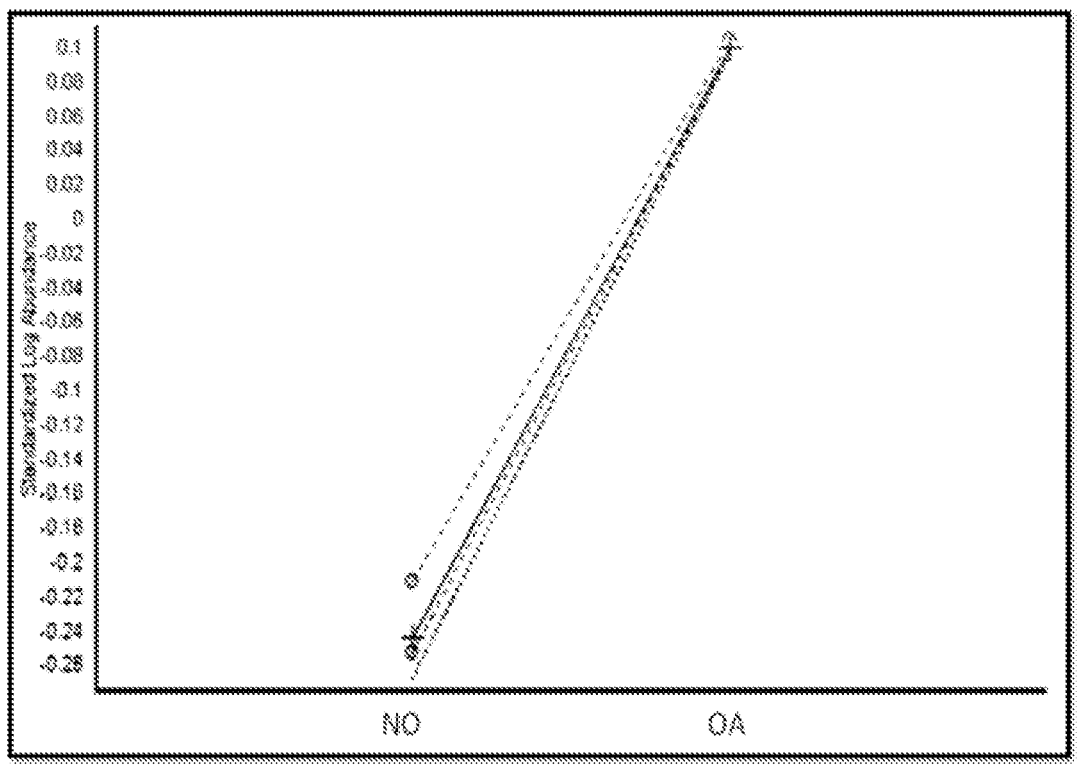

FIG. 2—shows a graphic view of fibulin-3 abundance modification based on the spot volume increase shown in FIG. 1B.

FIG. 3A—shows the result of a mass spectrometry analysis of tryptic fragments of the peptide of fibulin-3 recovered from spot 352 detailed in FIG. 1A, FIG. 1B and FIG. 2.

FIG. 3B—shows the sequence of human fibulin-3 containing the fragments shown in FIG. 3A.

Figure 4:
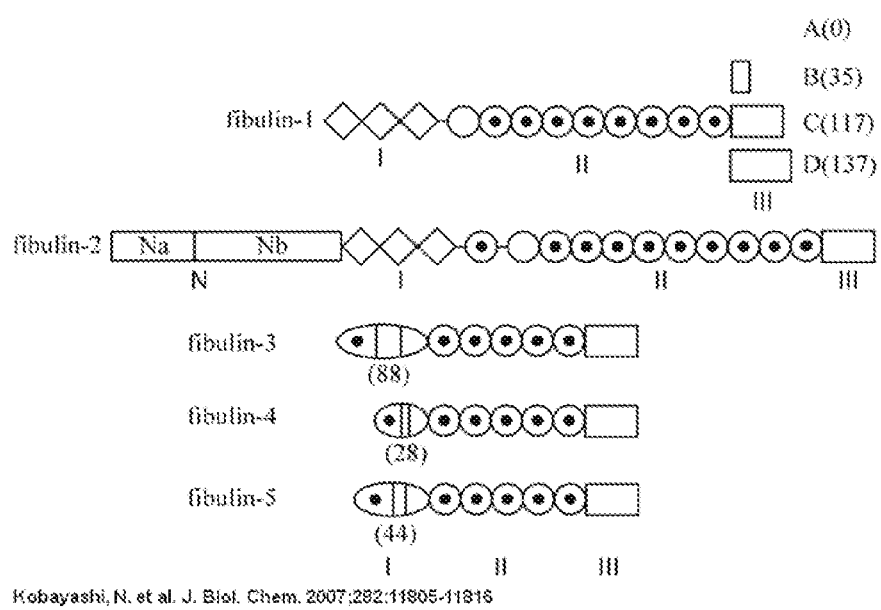

FIG. 4—shows the modular domain structure of the fibulin proteins.

FIG. 5—shows the protein sequence of SEQ ID No. 1.

FIG. 6—shows the protein sequence of SEQ ID No. 2.

Figure 7A:
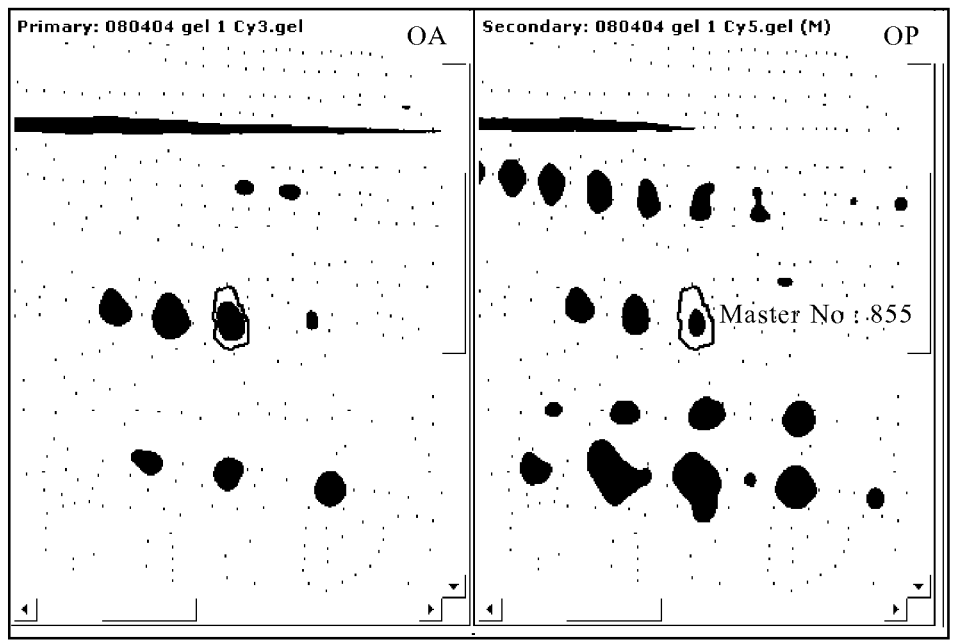

FIG. 7A—shows an enlargement of a portion of a 2D-DIGE map from osteoarthritis (OA) subjects (Cy3, left) and osteoporosis (OP) subjects (Cy5, right).

Figure 7B:
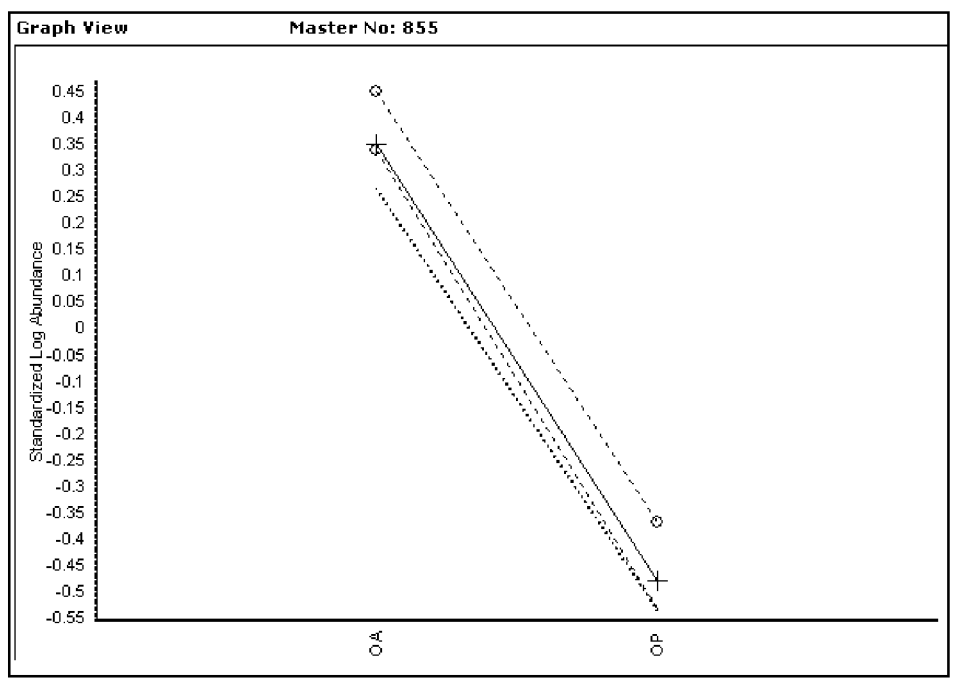

FIG. 7B—shows a graphic view of fibulin-3 abundance modification based on the spot volume increase shown in FIG. 7A.

Figure 8:
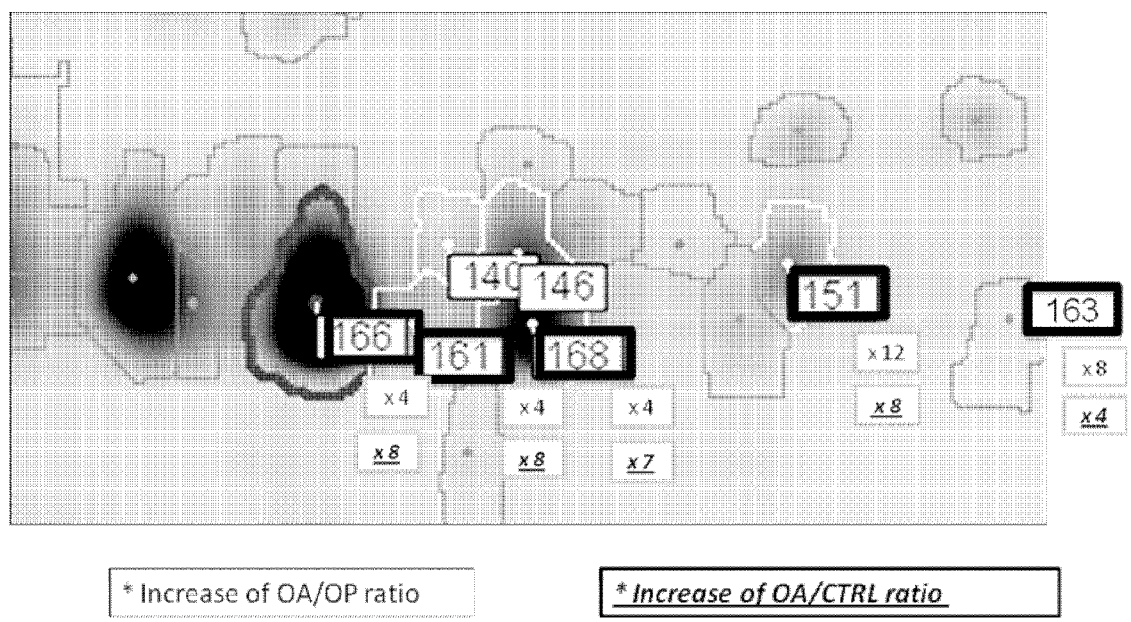

FIG. 8—shows an enhanced portion of 2D-DIGE gel obtained from proteins extracted from patients with severe osteoarthritis (OA), patients with osteoporosis (OP) and controls younger than 30 years (CTRL).

2D-DIGE (two dimensional difference gel electrophoresis—Marouga et al, (2005) Anal Bioanal Chem 382(3): 669-78) methodology is a powerful tool for investigating protein expression profiles in multiple sets of samples.

In the examples, 2D-DIGE was used to study the protein expression profiles in urine samples from subjects with serious osteoarthritis or osteoporosis and from healthy young subjects. Proteins in the samples to be compared were labelled with either Cy3 or Cy5 CyDye DIGE Fluors. The Cy2 CyDye DIGE Fluor was used to label a pooled sample comprising equal amounts of each of the samples within the study, and this used as an internal standard. The use of this internal standard ensured that all proteins present in the samples were represented, assisting both inter- and intra-gel matching.

Materials and Methods

Urine Samples Preparation

Urine samples were collected from 10 women undergoing hip replacement surgery due to severe osteoarthritis. Control samples were obtained from 5 healthy women (25.6±2.6 years) without articular degeneration. The urine samples were concentrated 100× by ultracentrifugation on Amicon Ultra-15 (Millipore, USA). Proteins were purified by precipitation using PlusOne 2D Clean-up kit (GE Healthcare, Sweden). Albumin depletion from urine samples was performed using affinity columns according to the Montage Albumin Deplete Kit (Millipore, USA) manual utilisation.

Labelling of Proteins with Cy3 and Cy5 Dyes

In all experiments, the purified proteins were labelled on lysine residues with Cy3 or Cy5 CyDye DIGE Fluors. The samples were minimal labelled which means that the ratio of dye to protein used was such that each protein molecule was labelled with only one dye molecule. Three gels were made as shown in Table 1. Proteins from different samples were labelled with Cy3 or Cy5 and loaded on the same gel. On the first and second gels, proteins from normal (NO) samples were labelled with Cy3 CyDye DIGE Fluor whereas protein from osteoarthritis (OA) samples were labelled with Cy5 CyDye DIGE Fluor. Conversely, on the third gel, proteins from NO samples were labelled with Cy5 CyDye DIGE Fluor and proteins from OA samples were labelled with Cy3 CyDye DIGE Fluor. An internal standard (MIX) comprising equal amounts of NO and OA samples was labelled with Cy2 CyDye DIGE Fluor and loaded on each gel.

TABLE 1

|  | Gel 1 | Gel 2 | Gel 3 |
| --- | --- | --- | --- |
| Cy3 | NO | NO | OA |
| Cy5 | OA | OA | NO |
| Cy2 | MIX | MIX | MIX |

Two-Dimensional Electrophoresis

Protein samples (37.5 µg) labelled with Cy3, Cy5 or Cy2 DIGE Fluor were separated by 2D electrophoresis using an IEF (ioselectric focusing) buffer (8 M urea, 2% CHAPS, 0.5% immobilized pH gradient [IPG] buffer, 1% DTT, and trace of bromophenol blue) which was loaded into an immobiline DryStrip (pH 3-10 NL, 24 cm) (GE Healthcare, Sweden). The first dimension isoelectric focusing was performed for 70,000 Vhr using a Protean IEF Cell (Biorad) at 20° C. Next, the gels were equilibrated for 12 minutes in equilibration buffer I (375 mM Tris-Cl [pH 8.8], 6 M urea, 20% glycerol, 2% SDS, and 130 mM DTT) and II (375 mM Tris-Cl [pH 8.8], 6 M urea, 20% glycerol, 2% SDS, and 135 mM IAA). The second dimension was run according to the Ettan DALTsix Electrophoresis Unit operating manual (GE Healthcare, Sweden). A 12.5% SDS-polyacrylamide slab gel (24 cm) was used for the second-dimension gel electrophoresis. The IPG strips were placed on the surface of the second-dimension gel. The gels were then placed in SDS electrophoresis buffer (25 mM Tris base, 192 mM glycine, 0.1% SDS) and run overnight at 1.5 W per gel.

Gels were scanned while still between two low-fluorescence glass plates using a Typhoon 9400 fluorescent scanner and saved in .gel format using ImageQuant software (GE Healthcare, Sweden). The excitation wavelengths for Cy3 and Cy5 are 550 nm and 645 nm, and the emission wavelengths are 570 nm and 670 nm for Cy3 and Cy5, respectively. The excitation/emission wavelength of Cy2 is around 489/505 nm. Image analysis was performed on DeCyder™ software (GE Healthcare, Sweden). Interesting spots with differential fluorescent intensity between Cy3 and Cy5 were picked out the gel, after post-staining with Coomassie Blue, in order to allow protein identification.

DeCyder 2D v6.5 software (GE Healthcare, Sweden) was used for the simultaneous comparison of abundance changes across sample groups. The DeCyder differential in-gel analysis (DIA) module generated ratios for each protein "spot" by comparing Cy3 and Cy5 signals to the Cy2 control signal. The DeCyder biological variation analysis module matched all protein spot maps from the gels and normalized the DIA-generated Cy3:Cy2 and Cy5:Cy2 ratios relative to the Cy2 signals for each resolved feature separately. This enabled the calculation of average abundance changes across all three samples within each test group, and the application of univariate statistical analyses (Student's t-test, ANOVA).

Proteins Identification

Protein spots were cut out of the polyacrylamide gel and washed twice for 5 minutes with an ammonium hydrogenocarbonate (50 mM)-acetonitrile mix (1:1). Gel spots were incubated in dithiothreitol (10 mM), $NH_4HCO_3$ (50 mM), for 40 min in a 56° C. water bath. Proteins in the gel spots were alkylated for 1 h in the dark with iodoacetamide (55 mM) in $NH_4HCO_3$ (50 mM). The gel spots were then washed twice with an ammonium hydrogenocarbonate (50 mM)-acetonitrile mix (1:1), dehydrated with acetonitrile, and then dried for 15 minutes at room temperature. The gel spots were then rehydrated for 10 minutes on ice with modified trypsin (10 ng/µl) in $NH_4HCO_3$ (25 mM) and then incubated overnight at 37° C. Hydrolysis of peptides was stopped in TFA (1%)-ACN (5%) solution. The gel spots were then sonicated twice for 1 minute in order to release protein fragments out of the isolated gel spots. Protein fragments in solution were freeze-dried. The identity of proteins was determined by tandem mass spectrometry (MS-MS spectrometry). The Mowse score (Pappin et al (1993) Curr Biol June 1; 3(6):327-32) gave the fidelity of identification.

Results

Proteins isolated from the urine samples and labelled with Cy3 or Cy5 were separated by two-dimensional electrophoresis. The first separation was performed with an isoelectric focusing range of pH 3-10 NL and a load of 37.5 μg of protein. 372 spots of proteins were matched between all gels. Spots with a modification of intensity between OA and NO with a ratio superior to 1.5 (t-test: p<0.05) were selected for protein identification using mass spectrometry. Table 2 shows the results of analysis of these spots, and details the size of the spot, the Mowse score (which is −10 log (P) where P is the probability that the observed match is a random event), the abundance ratio, the name of the protein identified in the spot and the accession number for the identified protein in the Swiss Prot database.

TABLE 2

| Spot n° | Sequence coverage (%) | Mowse score | Abundance ratio (OA/NO) | Protein description | Swiss-Prot Accession |
|---|---|---|---|---|---|
| 40 | 9 | 390 | 1.83 | Poly-Ig receptor (PIGR) | P01833 |
| 43 | 5 | 159 | 1.6 | Poly-Ig receptor (PIGR) | P01833 |
| 75 | 10 | 340 | −1.68 | Transferrin | P02787 |
| 219 | 11 | 334 | −1.7 | Kininogen-1 | P01042 |
|  | 6 | 55 |  | precursor Alpha 1 anti-trypsin (A1AT) | P01009 |
| 222 | 15 | 349 | −1.64 | Kininogen-1 | P01042 |
|  | 7 | 99 |  | precursor A1AT | P01009 |
| 223 | 13 | 405 | −1.89 | Kininogen-1 | P01042 |
|  | 16 | 311 |  | precursor A1AT | P01009 |
| 226 | 18 | 334 | −1.73 | A1AT | P01009 |
|  | 6 | 219 |  | Kininogen-1 precursor | P01042 |
| 262 | 13 | 368 | −1.91 | Kininogen-1 | P01042 |
|  | 6 | 61 |  | precursor A1AT | P01009 |
| 267 | 10 | 304 | −1.98 | Kininogen-1 precursor | P01042 |
| 269 | 5 | 143 | −1.83 | Kininogen-1 precursor | P01042 |
| 343 |  | 189 | 4.18 | Beta-actine |  |
| 348 | 21 | 192 | 2 | Zn-α-2-glycoprotein precursor | P25311 |
| 349 | 8 | 195 | −2.44 | Serpin B3 | P29508 |
| 351 | 6 | 115 | −5.84 | Serpin B1 | P30740 |
| 352 | 5 | 130 | 2.2 | Fibulin-3 | Q12805 |
|  |  | 73 |  | Apoptosis-inducing factor 2 (two proteins identified in the same spot) | Q9BRQ8 |
| 356 | 8 | 110 | 2.01 | Zn-α-2-glycoprotein precursor FIBULIN3 | P25311 Q12805 |
|  | 2 | 45 |  |  |  |
| 386 | 10 | 197 | 1.54 | GP36b | Q12907 |
| 398 | 5 | 187 | 2.28 | AMBP protein precursor | P02760 |
| 485 | 8 | 289 | −2.3 | Mannan-binding lectin serine protease 2 precursor | O00187 E.C 3.4.21.104 |

As can be seen from Table 2, various proteins with significant changes in concentration in samples from osteoarthritis compared to samples from normal subjects were identified. Some of the proteins identified are known to be implicated in the inflammatory process, for example, the kininogen precursor or alpha-1-antitrypsin. This observation coincides with the pathology of osteoarthritis.

A significant increase in the concentration of a specific fibulin-3 fragment was observed in osteoarthritis subjects compared to normal subject, as shown in Table 2 and FIGS. 1A and 1B. In FIG. 1A there is shown an enlargement of the area around spot 352 (indicated by one side of the double headed arrow) on the 2D-DIGE map of proteins extracted from urine from osteoarthritis subjects (right) compared to normal subjects (left). Spot 352 was shown by mass spectrometry to contain a fibulin-3 fragment. In FIG. 1B the same spot (spot 352) is represented by volume variation of the spot (indicated by the other head of the double headed arrow, equivalent to the spot of FIG. 1A) between samples from OA subjects (right) and NO subjects (left). A graphic view of the abundance modification based on the spot 352 volume increase is also shown in FIG. 2.

Tryptic fragments from spot 352 were identified by mass spectrometry analysis as shown in FIG. 3A. These fragments were identified as being fragments from the protein fibulin-3, as shown in FIG. 3B. FIG. 3B shows the protein sequence derived by the translation of the mRNA of human fibulin-3 and in bold the specific sequence identified by mass spectrometry. Each tryptic fragment studied was given a score which is −10 log(P), where P is the probability that the observed match is a random event. Individual ion scores >50 indicate identity or extensive homology. In the case of FIG. 3A the tryptic peptides scored 58 and 72 respectively indicating extensive homology.

In addition to the experiments comparing OA and NO subjects, further studies were undertaken to compare OA and osteoporosis (OP) subjects. In these studies urine samples obtained from four women with serious osteoporosis. Three gels were made, as shown in Table 3, to compare the OA and OP subjects. Proteins from different samples were labelled with Cy3 or Cy5 CyDye DIGE Fluor and loaded on gels as indicated in Table 3. An internal standard (MIX) comprising equal amounts of OA and OP samples was labelled with Cy2 CyDye DIGE Fluor and loaded on each gel. The first separation was performed with an isoelectric focusing range of pH 4-7 and a load of 37.5 μg of protein.

TABLE 3

|  | Gel 1 | Gel 2 | Gel 3 |
|---|---|---|---|
| Cy3 | OA | OA | OP |
| Cy5 | OP | OP | OA |
| Cy2 | MIX | MIX | MIX |

Analysis of the gels shows that the spot containing the fibulin-3 fragment (as described with reference to FIGS. 3A and 3B) shows a decrease of abundance in OP samples compared to OA samples with a ratio of 6.72. These results are illustrated in FIGS. 7A and 7B.

In a second experiment, proteins extracted from urine of osteoarthritic (OA) and control (NO) populations used in the initial experiment (described with reference to FIGS. 1 to 6) and from the urine of osteoporotic patients (OP) (described with reference to FIGS. 7A and 7B) were compared. Five gels were made as shown in Table 4. Proteins from different samples were labelled with Cy3 or Cy5 and loaded on the same gel. An internal standard (MIX) comprising equal amounts of NO, OA and OP samples was labelled with Cy2 CyDye DIGE Fluor and loaded on each gel. The first separation was performed with an isoelectric focusing range of pH 4-7 and a load of 37.5 μg of protein.

TABLE 4

|  | Gel 1 | Gel 2 | Gel 3 | Gel 4 | Gel 5 |
|---|---|---|---|---|---|
| Cy3 | OA | OP | NO | NO | OA |
| Cy5 | OP | OA | OA | OP | NO |
| Cy2 | MIX | MIX | MIX | MIX | MIX |

Analysis of the five gels showed that spots containing the fragment of fibulin-3 (as described with reference to FIGS. 3A and 3B) show an abundance modification with a ratio comprised between 4-8 for OA/NO comparison and 4-12 for OP/OA comparison, depending on the spot containing the fragment. Indeed, we have identified five different forms of the fibulin-3 which differently discriminate osteoarthritic and osteoporotic patients as illustrated in FIG. 8.

The appearance of several spots containing fragments of fibulin-3 suggests that the protein is present in various forms in the urinary proteome. The sequence could be modified specifically by phosphorylation, glycosylation or other post-traductional modifications resulting of a pathophysiological mechanism. All the identified forms are increased in OA samples compared to OP and NO samples. However, some forms appear to be more increased regarding the spot observed and could be more concerned by the pathologic process. Selected fragment discriminates patients with osteoarthritis from those with osteoporosis. This could not be identified by a person skilled in the art.

This data shows that the increased abundance of the fragment of fibulin-3 is a specific event occurring in osteoarthritic disease. Furthermore, a decrease in the level of this protein is seen in samples from subjects with osteoporosis samples compared to those from subjects with osteoarthritis. Note that different ratios were found between multiple experiments because the internal standard was changed for each of them.

In FIG. 8, Proteins were separated on a linear pH gradient (pH 4-7) IPG strip, followed by a 12.5% SDS-PAGE. Selected spots (▬) contain fragments of fibulin-3 identified by mass spectrometry. Modified ratio of fibulin-3 content is annotated under the corresponding spot.

Fibulins are a family of five extracellular matrix proteins characterized by modular domain structures as depicted in FIG. 4. The general fibulins modular domain structure comprises tandem arrays of epidermal growth factor-like (EGF-like) modules (domain II, represented by circles) and a C-terminal fibulin-type module (domain III, represented by rectangles). Some of the EGF-like modules possess a consensus motif for calcium binding (cbEGF-like module represented by circles with black dots). Fibulin-1 and fibulin-2 comprise anaphylatoxin-like modules (domain I, represented by diamonds). Domain N, which is unique to fibulin-2, can be subdivided into a Cys-rich segment (Na) and a Cys-free segment (Nb). Fibulin-3, fibulin-4, and fibulin-5 have a modified cbEGF-like module at their N-terminus. This modified cbEGF-like module has an extra $Cys^5$-$Cys^6$ loop at the beginning of the module and a long linker region between $Cys^2$-$Cys^4$ and $Cys^5$-$Cys^6$ loops. The residues between $Cys^4$ and $Cys^5$ are shown in parentheses. Four different alternative splice variants are reported for human fibulin-1, shown as variants A-D, and the numbers in parentheses indicate residues of domain III.

Fibulin-1 (703 AA; 77.2 kDa) and Fibulin-2 (1184 AA; 126.5 kDa) are localized in basement membranes, elastic fibers, and other connective tissue structures. Fibulin-4 (443 AA; 49.4 kDa) was identified through its sequence homology to fibulin-1, fibulin-2, and fibulin-3 and independently as a protein interacting with a mutant form of the tumor suppressor protein p53. Fibulin-5 (48 AA; 50.2 kDa) was first characterized as a gene strongly expressed in large blood vessels during embryonic development and highly up-regulated upon vascular injury.

Fibulin-3 is also known as EFEMP1 protein and has SWISS-PROT accession number Q12805. Fibulin-3 is a protein comprising 493 amino acids and has a molecular weight of about 54.6 kDa. Fibulin-3 was originally identified by subtractive cDNA cloning from a Werner syndrome fibroblast library and shown to be expressed at increased levels in serum-deprived fibroblasts. As with all other fibulins, fibulin-3 is present in blood vessels of different sizes and is capable of inhibiting vessel development and angiogenesis both in vitro and in vivo. Fibulin-3 is expressed in cartilage and bone structures during development and may play a role in the skeletal system. Fibulin-3 is known to be intimately associated with TIMP-3, an inhibitor of metalloproteinase involved in the pathogenesis of osteoarthritis (Klenotic et al., J Biol Chem, 2004. 279(29): p. 30469-73; Sahebjam et al., Arthritis Rheum, 2007. 56(3): p. 905-9; Kevorkian et al., Arthritis Rheum, 2004. 50(1): p. 131-41). The results presented herein show that the fibulin-3 fragment described with reference to Seq ID No: 1, FIG. 3B and FIG. 5 is present in an increased amount in biological sample, such as urine, of subjects with osteoarthritis. The data also shows that a decreased level of the fibulin-3 fragment may be diagnostic of osteoporosis as well as osteoarthritis. Thus, peptides having the sequence of Seq ID No: 1, or substantially the sequence of Seq ID No: 1, or a part thereof, may be used as biomarkers for osteoarthritis, osteoporosis and/or other ageing-related diseases.

The invention claimed is:

1. A method of determining the osteoarthritis status of a subject, and/or the status of another ageing-related disease in a subject, comprising the steps of:
   (i) determining the concentration in a biological sample of a free fragment consisting of amino acid sequence SEQ ID NO:1;
   (ii) comparing the free fragment concentration determined in step (i) with one or more reference values to determine the osteoarthritis status and/or the status of another ageing-related disease in the subject.

2. A method of diagnosing osteoarthritis and/or another ageing-related disease in a subject, comprising the steps of:
   (i) determining the concentration in a biological sample of a free fragment consisting of amino acid sequence SEQ ID NO:1;
   (ii) comparing the peptide concentration determined in step (i) with one or more reference values to determine the osteoarthritis status and/or the status of another ageing-related disease in the subject.

3. A method of determining the prognosis for a subject with osteoarthritis and/or another ageing-related disease, comprising the steps of:
   (i) determining the concentration in a biological sample of a free fragment consisting of amino acid sequence SEQ ID NO:1;
   (ii) comparing the free fragment concentration determined in step (i) with one or more reference values to determine the osteoarthritis status and/or the status of another ageing-related disease in the subject.

4. The method of claim 1, wherein, prior to and after the following steps, the steps (i) and (ii) are performed:
   (A) administering a treatment for osteoarthritis and/or another ageing related disease to the subject;
   (B) providing a biological sample from the subject after administration of the treatment.

5. The method of claim 1 wherein the biological sample is selected from the group comprising urine, whole blood, blood serum, blood plasma, synovium, sweat, cerebrospinal fluid, mucous, saliva, lymph, bronchial aspirates and milk.

6. The method of claim 1 wherein the concentration of the free fragment is determined by using an immunoassay.

7. The method of claim 1 wherein the reference value is the concentration of the free fragment in one or more normal subjects.

8. A kit for use in determining the osteoarthritis status, or the status of another ageing-related disease, in a subject comprising at least one agent for determining the concentration of a free fragment consisting of amino acid sequence of Seq ID No:1, in a biological sample.

9. The kit according to claim 8 wherein the agent is selected from the group comprising an enzyme, an antibody, a protein probe, a metabolite or any other suitable composition.

10. The kit according to claim 8 wherein the agent comprises two antibodies directed to different epitopes on the free fragment.

11. The kit according to claim 10 for use in determining the concentration of the free fragment by using a sandwich immunoassay.

12. An isolated free fragment which consists of amino acid sequence of SEQ ID NO: 1, or its amide, or a salt thereof.

* * * * *

SEQUENCE LISTING

<160> NUMBER OF SEQ ID NOS: 2

<210> SEQ ID NO 1
<211> LENGTH: 57
<212> TYPE: PRT
<213> ORGANISM: Homo sapiens

<400> SEQUENCE: 1

Thr Cys Gln Asp Ile Asn Glu Cys Glu Thr Thr Asn Glu Cys Arg Glu
1               5                   10                  15

Asp Glu Met Cys Trp Asn Tyr His Gly Gly Phe Arg Cys Tyr Pro Arg
            20                  25                  30

Asn Pro Cys Gln Asp Pro Tyr Ile Leu Thr Pro Glu Asn Arg Cys Val
        35                  40                  45

```
Cys Pro Val Ser Asn Ala Met Cys Arg
        50                  55
```

<210> SEQ ID NO 2
<211> LENGTH: 493
<212> TYPE: PRT
<213> ORGANISM: Homo sapiens

<400> SEQUENCE: 2

```
Met Leu Lys Ala Leu Phe Leu Thr Met Leu Thr Leu Ala Leu Val Lys
1               5                   10                  15

Ser Gln Asp Thr Glu Glu Thr Ile Thr Tyr Thr Gln Cys Thr Asp Gly
                20                  25                  30

Tyr Glu Trp Asp Pro Val Arg Gln Gln Cys Lys Asp Ile Asp Glu Cys
            35                  40                  45

Asp Ile Val Pro Asp Ala Cys Lys Gly Gly Met Lys Cys Val Asn His
        50                  55                  60

Tyr Gly Gly Tyr Leu Cys Leu Pro Lys Thr Ala Gln Ile Ile Val Asn
65                  70                  75                  80

Asn Glu Gln Pro Gln Gln Glu Thr Gln Pro Ala Glu Gly Thr Ser Gly
                85                  90                  95

Ala Thr Thr Gly Val Val Ala Ala Ser Ser Met Ala Thr Ser Gly Val
                100                 105                 110

Leu Pro Gly Gly Gly Phe Val Ala Ser Ala Ala Val Ala Ala Gly Pro
            115                 120                 125

Glu Met Gln Thr Gly Arg Asn Asn Phe Val Ile Arg Arg Asn Pro Ala
130                 135                 140

Asp Pro Gln Arg Ile Pro Ser Asn Pro Ser His Arg Ile Gln Cys Ala
145                 150                 155                 160

Ala Gly Tyr Glu Gln Ser Glu His Asn Val Cys Gln Asp Ile Asp Glu
                165                 170                 175

Cys Thr Ala Gly Thr His Asn Cys Arg Ala Asp Gln Val Cys Ile Asn
                180                 185                 190

Leu Arg Gly Ser Phe Ala Cys Gln Cys Pro Pro Gly Tyr Gln Lys Arg
            195                 200                 205

Gly Glu Gln Cys Val Asp Ile Asp Glu Cys Thr Ile Pro Pro Tyr Cys
210                 215                 220

His Gln Arg Cys Val Asn Thr Pro Gly Ser Phe Tyr Cys Gln Cys Ser
225                 230                 235                 240

Pro Gly Phe Gln Leu Ala Ala Asn Asn Tyr Thr Cys Val Asp Ile Asn
                245                 250                 255

Glu Cys Asp Ala Ser Asn Gln Cys Ala Gln Gln Cys Tyr Asn Ile Leu
                260                 265                 270

Gly Ser Phe Ile Cys Gln Cys Asn Gln Gly Tyr Glu Leu Ser Ser Asp
            275                 280                 285

Arg Leu Asn Cys Glu Asp Ile Asp Glu Cys Arg Thr Ser Ser Tyr Leu
290                 295                 300

Cys Gln Tyr Gln Cys Val Asn Glu Pro Gly Lys Phe Ser Cys Met Cys
305                 310                 315                 320

Pro Gln Gly Tyr Gln Val Val Arg Ser Arg Thr Cys Gln Asp Ile Asn
                325                 330                 335

Glu Cys Glu Thr Thr Asn Glu Cys Arg Glu Asp Glu Met Cys Trp Asn
            340                 345                 350

Tyr His Gly Gly Phe Arg Cys Tyr Pro Arg Asn Pro Cys Gln Asp Pro
```

```
                 355                 360                 365
Tyr Ile Leu Thr Pro Glu Asn Arg Cys Val Cys Pro Val Ser Asn Ala
        370                 375                 380

Met Cys Arg Glu Leu Pro Gln Ser Ile Val Tyr Lys Tyr Met Ser Ile
385                 390                 395                 400

Arg Ser Asp Arg Ser Val Pro Ser Asp Ile Phe Gln Ile Gln Ala Thr
                405                 410                 415

Thr Ile Tyr Ala Asn Thr Ile Asn Thr Phe Arg Ile Lys Ser Gly Asn
                420                 425                 430

Glu Asn Gly Glu Phe Tyr Leu Arg Gln Thr Ser Pro Val Ser Ala Met
            435                 440                 445

Leu Val Leu Val Lys Ser Leu Ser Gly Pro Arg Glu His Ile Val Asp
        450                 455                 460

Leu Glu Met Leu Thr Val Ser Ser Ile Gly Thr Phe Arg Thr Ser Ser
465                 470                 475                 480

Val Leu Arg Leu Thr Ile Ile Val Gly Pro Phe Ser Phe
                485                 490
```